United States Patent [19]

Nakada et al.

[11] Patent Number: 5,837,527
[45] Date of Patent: Nov. 17, 1998

[54] β-FRUCTOFURANOSIDASE ITS PREPARATION AND USES

[75] Inventors: Tetsuya Nakada; Hiroto Chaen; Toshiyuki Sugimoto, all of Okayama, Japan

[73] Assignee: Kabushiki Kaisha Hayashibara Seibutsu Kagaku Kenkyujo, Okayama, Japan

[21] Appl. No.: 941,552

[22] Filed: Sep. 30, 1997

Related U.S. Application Data

[62] Division of Ser. No. 763,885, Dec. 11, 1996, Pat. No. 5,753,469.

[30] Foreign Application Priority Data

Dec. 18, 1995 [JP] Japan ................................. 7-347543

[51] Int. Cl.[6] ............................. C12N 1/20; C12N 9/26; C12P 19/14
[52] U.S. Cl. ................... 435/252.5; 435/832; 435/837; 435/200; 435/201; 435/96; 435/97; 435/99; 435/100; 435/101
[58] Field of Search ................. 435/252.5, 832, 435/837, 200, 201, 96, 99, 97, 100, 101

[56] References Cited

U.S. PATENT DOCUMENTS 4,487,198 12/1984 Miyake et al. .
4,521,252 6/1985 Miyake et al. .

FOREIGN PATENT DOCUMENTS

| 0 470 331 A1 | 2/1992 | European Pat. Off. . |
| 58-023799 | 2/1983 | Japan . |
| 58-072598 | 4/1983 | Japan . |
| 4-200386 | 7/1992 | Japan . |
| 53 009 390 A | 1/1998 | Japan . |

OTHER PUBLICATIONS

Sneath, Peter H. ed. et al., "Bergey's manual of systematic bacteriology" vol. 2, Williams & Wilkins, 1986.

Fujita, Koki et al., "Purification and some properties of β–Fructofuranosidase I from arthrobacter sp. K–1.", Agric. Biol. Chem., vol.54, No. 4, pp. 913–919 (1990).

Hasegawa, Takeji ed., "Classification and identification of microorganism.", Japan Scientific Societies Press, (1985).

Patent Abstracts of Japan, vol. 016, No. 528, 29 Oct. 1992 (JP 04 200386 A).

*Primary Examiner*—Francisco C. Prats
*Attorney, Agent, or Firm*—Browdy and Neimark

[57] ABSTRACT

A β-fructofuranosidase with a molecular weight of 49,000±5,000 daltons on SDS-PAGE, an isoelectric point of 4.6±0.5, an optimum pH of about 5.5–6.0, and an optimum temperature of about 50° C. in the presence of calcium ion. The enzyme acts on saccharides with a β-fructofuranosidic linkage and other substances including other saccharides, sugar alcohols, and alcohols to produce fructosyl-transferred saccharides in a relatively high yield.

3 Claims, 4 Drawing Sheets

—○—: Acetate buffer

—●—: Tris-HCl buffer

—△—: Acetate buffer (in the presence of 5 mM calcium chloride)

—▲—: Tris-HCl buffer (in the presence of 5 mM calcium chloride)

—O— : Acetate buffer (in the absence of calcium chloride)

—△— : Acetate buffer (in the presence of 5 mM calcium chloride)

—O—: Acetate buffer (in the absence of calcium chloride)

β-FRUCTOFURANOSIDASE ITS PREPARATION AND USES

This application is a divisional of application Ser. No. 08/763,885, filed Dec. 11, 1996, now U.S. Pat. No. 5,753,469.

BACKGROUND OF THE INVENTION

1. Field of the Invention

The present invention relates to a novel β-fructofuranosidase with a relatively high fructosyl-transferring activity, its preparation and uses.

2. Description of the Prior Art

Fructosyl-transferred saccharides such as xylosylfructoside and lactosucrose, which are produced by the saccharide-transferring reaction using β-fructofuranosidase (EC 3.2.1.26) or fructosyltransferase to act on sucrose and other saccharide(s) as a substrate, have the properties of an anti-cariogenicity and a growth-promoting activity for bifid bacteria. Therefore, these oligosaccharides are attracting much attention from the food and pharmaceutical fields.

Conventionally known β-fructofuranosidases, which form the fructosyl-transferred saccharides, are those derived from microorganisms of the species Arthrobacter sp. K-1 and *Bacillus megaterium* (IFO 13498).

"*Agricultural and Biological Chemistry*", Vol. 54, No.4, pp.913–919 (1990) reports that the β-fructofuranosidase of Arthrobacter sp. K-1 has an optimum pH of 6.5–6.8. However, it is not suitable because under the pH range the browning reaction of saccharides readily occurs at temperatures used in the industrial-scale enzymatic reactions. Particularly, the tendency is more critical in the fructose-forming reaction, and this may give an overload to the decolorization steps for purifying saccharides in reaction mixtures. As is disclosed in Japanese Patent Laid-Open No.200,386/92, the β-fructofuranosidase of *Bacillus megaterium* IFO 13498 has an optimum pH of 6.0. Under the pH condition, reaction mixtures may be less colored. However, the optimum temperature is low as 40°–45° C. so that a bacterial contamination may occur when the enzymatic reactions are carried out at around the temperatures.

SUMMARY OF THE INVENTION

The present invention provides a β-fructofuranoside, which has a relatively high fructosyl-transferring activity and is suitably used on an industrial scale, preparation of fructosyl-transferred saccharides using the enzyme, and uses of the saccharides.

The present inventors widely screened microorganisms which form a novel β-fructofuranosidase which has a relatively high saccharide-transferring activity and optimum temperature, and an optimum pH of a slightly acidic pH which stabilizes saccharides.

As a result, they found that a novel microorganism of Bacillus sp. V230 (FERM BP-5054), isolated from a soil in Okayama, Japan, forms the desired β-fructofuranosidase, and established the process for producing saccharide compositions containing fructosyl-transferred saccharides, which comprises allowing the enzyme to act on solutions containing sucrose and other saccharides, and compositions containing these saccharide compositions.

BRIEF EXPLANATION OF THE ACCOMPANYING DRAWINGS

DETAILED DESCRIPTION OF THE INVENTION

Figure 1:
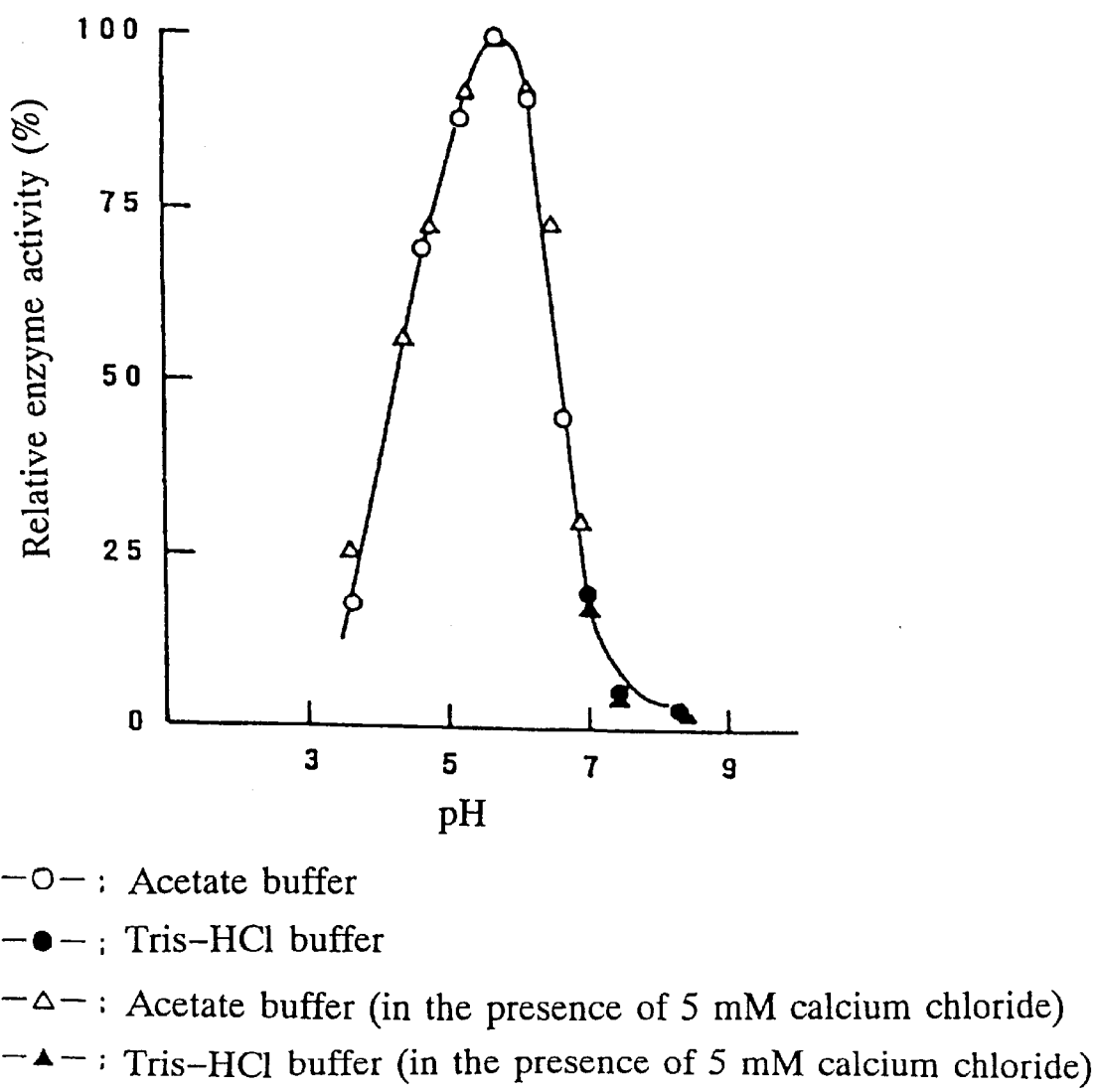
FIG. 1 shows the influence of pH on the activity of the present β-fructofuranosidase.

The present inventors widely screened microorganisms which produce a novel β-fructofuranosidase. As a result, they isolated a novel microorganism, Bacillus sp. V230 (FERM BP-5054), from a soil in Okayama, Japan, which forms the desired β-fructofuranosidase.

In accordance with the method in "Biseibutsu-no-Bunrui-to-Dotei (Classification and Identification of Microorganisms)", edited by Takeji Hasegawa, published by Japan Scientific Societies Press, Tokyo, Japan (1985), the present inventors identified the microorganism as one of the genus Bacillus and named it Bacillus sp. V230 (FERM BP-5054). The results are as follows:

A. Morphology (1) Characteristics of cells when incubated at 27° C. for a day in meat extract agar plate
  Usually existing in a rod form of 1.0–1.5×3.0–7.5 μm;
  Existing in a single form but uncommonly existing in a coupled- or linked-form;
  Motile with rounded flagella;
  Non-acid fast;
  Gram-variable;
  Not accumulating poly-β-hydroxybutyrate; and
  Occasionally, forming endospore when cultured for 4 days.

(2) Characteristics of cells when incubated at 27° C. for a day in agar plate of potato extract, peptone, and glucose
  Usually existing in a rod form of 0.9–1.5×2.7–6.0 μm;
  Existing in a single form but uncommonly existing in a coupled- or linked-form;
  Motility: Positive;
  Gram-variable;
  Forming endospore;
  Forming spores in the cellular edge without swelling; and
  Spore size: 0.8–1.0×1.0–1.6 μm in an oval form;
  Forming spores even when cultured in a soil extract medium.

B. Cultural property (1) Characteristics of colony formed when incubated at 27° C. in meat extract agar plate
  Shape: Circular colony, an about 1.0–1.5 mm in diameter when cultured for a day, and an about 1.5–3 mm in diameter when cultured for 3 days;
  Rim: Entire;
  Projection: Upsurged;
  Gloss: Dull gloss;
  Surface: Plain or verruciform;
  Transparency: Semitransparent or opaque; and
  Color: Creamy;

(2) Characteristics of colony formed when incubated at 27° C. in meat extract agar slant
  Growth: Good;
  Shape: Thread-like; projected slightly; plain surface, moistened gloss or dull gloss; semitransparent; and creamy; and (3) Not liquefying gelatin when stab-cultured at 27° C. in meat extract gelatin.

C. Physiological properties
  (1) Reduction of nitrate: Positive
  (2) Denitrification reaction: Negative
  (3) Methyl red test: Negative
  (4) VP-test: Negative
  (5) Formation of indole: Negative
  (6) Formation of hydrogen sulfide: Negative
  (7) Hydrolysis of starch: Positive
  (8) Hydrolysis of casein: Negative
  (9) Accumulation of poly-β-hydroxybutyrate: Negative
  (10) Hydrolysis of procatec acid: Negative
  (11) Utilization of citric acid: Negative
  (12) Utilization of inorganic nitrogen source: Utilizing ammonium salts and nitrates;
  (13) Formation of pigment: Negative
  (14) Formation of fluorescent pigment: Negative
  (15) Urease: Positive
  (16) Oxidase: Positive
  (17) Catalase: Positive
  (18) Growth conditions: Growing at a pH of 5–8 and a temperature of 15°–45° C.;
  (19) Oxygen requirements: Aerobic
  (20) Utilization of carbon source and acid formation

| Carbon source | Utilization | Acid formation |
| --- | --- | --- |
| D-Glucose | + | + |
| D-Galactose | + | + |
| D-Mannose | + | + |
| D-Fructose | + | + |
| L-Arabinose | + | + |
| D-Xylose | + | + |
| L-Rhamnose | + | + |
| Maltose | + | + |
| Sucrose | + | + |
| Lactose | + | − |
| Trehalose | + | + |
| Raffinose | + | + |
| Sorbitol | + | + |
| Mannitol | + | + |
| Dulcitol | − | − |
| Glycerol | − | − |
| Dextrin | + | + |

(21) Decarboxylase test on amino acid Negative to L-lysine, L-arginine, and L-ornithine;
  (22) Utilization of amino acid Utilizing sodium L-glutamate, sodium L-aspartate, L-arginine, L-tryptophane, L-histidine, L-valine, and D-alanine;
  (23) DNase: Negative;
  (24) Formation of 3-ketolactose: Negative;
  (25) Mol % guanine (G) plus cytosine (C) of DNA: 41%; and
  (26) Diamino acid of cell wall: meso-diaminopimelic acid.

The microorganism with these bacteriological properties was compared with those of conventionally known microorganisms with reference to "Bergey's Manual of Systematic Bacteriology", Vol.2 (1986). As a result, it was revealed that the microorganism was identified as one of the genus Bacillus because it requires oxygen and forms endospores, though the gram stain is variable. The microorganism is similar to those of the species Bacillus megaterium based on those properties, but it is distinguishable from them by the fact that it forms internal spores at its cellular edges, does not hydrolyze casein, does not utilize citric acid, and does not grow at 10° C.

Based on these data, the present inventors named this microorganism "Bacillus sp. V230", and deposited it on Mar. 24, 1995, in the Fermentation Research Institute, Agency of Industrial Science and Technology, Ibaraki, Japan. The deposit of the microorganism was accepted by the institute and has been maintained under the accession number of FERM BP-5054.

The microorganism and its mutants can be used in the present invention.

Any nutrient culture media can be used in the present invention as long as the microorganisms used in the present invention grow therein and produce the present enzyme: For example, synthetic- and natural-nutrient culture media can be used as the nutrient culture media. Any carbon-containing substances can be used in the invention as carbon sources as long as the microorganisms utilize them: For example, saccharides such as sucrose, lactose, maltose, dextrin, and starch, as well as saccharide-containing products such as molasses and yeast extracts, can be used as the carbon sources. The concentrations of these carbon sources in nutrient culture media are selectively chosen depending on the types of carbon sources. For example, a recommendable sucrose concentration is usually 20 w/v % or lower, more particularly, 5 w/v % or lower in view of the microorganisms' growth and proliferation. The nitrogen sources usable in the present invention are, for example, inorganic nitrogen-containing compounds such as ammonium salts and nitrates; and organic nitrogen-containing compounds such as urea, corn steep liquor, casein, peptone, yeast extract, and beef extract. The inorganic ingredients usable in the present invention are, for example, calcium salts, magnesium salts, potassium salts, sodium salts, phosphates, and other salts of manganese, zinc, iron, copper, molybdenum and cobalt.

The cultivation of microorganisms usable in the present invention is conducted under aerobic conditions at a temperature of, usually, 15°–45° C., preferably, 25°–37° C.; and a pH of 5–8, preferably, 5.5–7.5. The cultivation time for micro-organisms used in the present invention is one, which is longer than that required for the microorganisms' proliferation, preferably, 5–100 hours. The concentration of the dissolved oxygen (DO) in nutrient culture media is not specifically restricted, preferably, it is in the range of 0.5–20 ppm. The concentration can be kept within the range by controlling the aeration rate, stirring ratio, supplementing oxygen rate, and increasing the inner pressure of fermenters. The cultivation is carried out in a batch-wise or a continuous manner.

After completion of the microorganisms' culture, collect the present enzyme. Since the activity of the present enzyme is found in cell-free nutrient culture media, the media can be collected and used as a crude enzyme. The intact cultures can be also used as a crude enzyme. Conventional liquid-solid separation methods can be used to remove cells from the cultures. For example, methods to directly centrifuge the cultures and those to filtrate the cultures with pre-coat filters or to separate cells by membrane filtration using plain filters or follow fibers can be selectively used. The resulting cell-free cultures can be used intact as a crude enzyme solution and, preferably, used after concentration. The concentration methods usable in the present invention are, for example, salting out using ammonium sulfate, sedimentation using acetone and/or alcohol, and concentration using membranes such as plain filters and follow fibers.

Crude enzymes in the form of a cell-free culture and their concentrates can be immobilized by conventional methods such as conjugation methods using ion exchangers, covalent bonding and absorption using resins and/or membranes, and inclusion methods using high-molecular weight substances.

Crude enzymes can be used intact or after purification. For example, cell-free cultures are salted out with ammonium sulfate, and the concentrated crude enzymes are dialyzed, and purified successively on anion exchange column chromatography using "DEAE-TOYOPEARL®", an anion exchanger commercialized by Tosoh Corporation, Tokyo, Japan, hydrophobic column chromatography using "BUTYL-TOYOPEARL®", a hydrophobic resin commercialized by Tosoh Corporation, Tokyo, Japan, and anion exchange column chromatography using "DEAE-TOYOPEARL®" to obtain an enzyme preparation exhibiting an electrophoretically single protein band.

The present β-fructofuranosidase thus obtained has the following physicochemical properties:

(1) Action Hydrolyzing the β-fructofuranosidic linkage in sucrose, raffinose, and erlose to release fructose; Catalyzing the transferring of β-fructofuranosyl residue from those saccharides as a donor, having the β-fructofuranosidic linkage, to an acceptor selected from other saccharides, sugar alcohols, and alcohols;

(2) Molecular weight 49,000±5,000 daltons on SDS-PAGE;

(3) Isoelectric point (pI) 4.6±0.5 on isoelectrophoresis using an ampholyte;

(4) Optimum pH About 5.5–6.0 when incubated at 40° C. for 10 min;

(5) Optimum temperature About 45° C. and about 50° C. in the absence of and in the presence of calcium ion, respectively, when incubated at pH 6.0 for 10 min;

(6) pH Stability About 5.0–8.0 when incubated at 4° C. for 24 hours;

(7) Thermal stability Stable up to about 45° C. when incubated at pH 6.0 for an hour; and (8) Inhibition Being inhibited by one mM $Cu^{++}$, $Pb^{++}$, $Fe^{++}$, $Fe^{+++}$ or $Hg^{++}$.

The activity of β-fructofuranosidase according to the present invention is assayed as follows: Add 0.2 ml of an enzyme solution to 5 ml of an aqueous solution (pH 6.0) consisting of 1.0 w/v % sucrose, 20 mM acetate buffer, and 5 mM calcium chloride. Incubate the mixture at 40° C. for 10 min, add the Somogyi copper solution to suspend the reaction, and assay the reducing power by the Somogyi-Nelson's method. As a control, provide an enzyme solution pre-heated to inactivate the enzyme at 100° C. for 10 min, and assay the reducing power similarly as above. One unit activity of the enzyme is defined as the amount of enzyme that increases the reducing power of 2 $\mu$mol glucose per minute when assayed on the above assay.

The present β-fructofuranosidase acts on sucrose to decompose into glucose and fructose moieties, but does not substantially cause an intermolecular transfer reaction between sucrose molecules even at a higher sucrose concentration, and does not substantially form oligosaccharides with a higher molecular weight than sucrose. While the enzyme forms xylosylfructoside, galactosylfructoside, lactosylfructoside (lactosucrose), maltosylfructoside (erlose), and isomaltosyl-fructoside when acts on both sucrose as a saccharide donor and other saccharides as an acceptor such as reducing saccharides including xylose, galactose, lactose, maltose, and isomaltose to transfer fructosyl residues to the reducing saccharides. When used as a saccharide acceptor non-reducing disaccharides consisting of glucose units such as trehalose and neotrehalose, the present enzyme forms fructosyltrehalose and fructosyl-neotrehalose, respectively. In addition to mono and disaccharides, higher oligosaccharides such as xylooligo-saccharides, galactooligosaccharides, maltooligosaccharides, and isomaltooligosaccharides, and sugar alcohols such as sorbitol and maltitol can be used as acceptors. One or more of these acceptors can be selectively used in combination. In addition to sucrose, other oligosaccharides with the β-fructofuranosidic linkage such as raffinose and erlose can be used as the saccharide donor.

The substrate concentration used in the fructosyl-transferring reaction to form saccharides using the present β-fructofuranosidase is not specifically restricted, and a concentration of 10 w/w % (the wording "w/w %" will be abbreviated as "%" unless specified otherwise) or more, preferably, 20–60%, can be suitably used. The reaction temperature used in the present invention is one which does not inactivate the present enzyme, i.e. a temperature of up to about 60° C., preferably, about 50°–55° C. The pH is controlled to a pH of about 3.5–8.0, preferably, about 4.5–6.5. The reaction time is selectively chosen depending on the enzymatic conditions. Usually, the present enzyme is used in an amount of about 0.1–50 units/g substrate, on a dry solid basis (d.s.b.), and the reaction time is about 0.1–100 hours.

The yield of fructosyl-transferred saccharides varies depending on the substrate concentration, the type of acceptors, and the reaction conditions for the present enzyme. For example, the highest possible yield of lactosucrose is about 40% when used 20% sucrose and 20% lactose.

The resulting reaction mixtures are filtered and centrifuged to remove insoluble substances in a conventional manner, and the mixtures are purified on decolonization and desalting with ion exchangers in H- and OH-form. The purified solutions are concentrated into syrupy products and, if necessary, further dried into powdery products.

To increase the content of transferred saccharides, they are separated from the reaction mixtures and purified into compositions rich in fructosyl-transferred saccharides. The methods suitably used for such purposes include a yeast fermentation method to remove monosaccharides using an invertase defective yeast, an alkali-treating method to decompose reducing saccharides by heating after alkalinizing the reaction mixtures, and a separation method to remove contaminating saccharides on membrane filtration and column chromatography. Particularly, the column chromatography using a strong-acid cation exchange resin as disclosed in Japanese Patent Laid-Open No.23,799/83 and 72,598/83 can be advantageously used on an industrial scale to remove contaminating saccharides from the reaction mixtures to obtain fractions containing the objective compositions rich in fructosyl-transferred saccharides. In this case, any conventional methods such as fixed-bed, moving-bed, and quasi-moving methods can be used.

Solutions free of contaminating saccharides are filtered and centrifuged to remove impurities in a conventional manner, and the supernatants are purified on decolorization using an activated charcoal and on desalting using ion exchangers in H- and OH-form, and concentrated into syrupy products. If necessary, the syrupy products can be dried by spraying into powdery products.

Usually, the saccharide compositions contain fructosyl-transferred saccharides, produced by the present β-fructofuranosidase, in an amount of 5% or more, preferably, 10% or more.

The saccharide compositions thus obtained have the following satisfactory properties: a good taste and sweetness, osmosis-controlling ability, moisture-retaining ability or humectancy, gloss-imparting ability, crystallization-preventing ability, retrogradation-preventing ability, anti-cariogenicity, growth-promoting activity for bifid bacteria, and mineral absorption-promoting activity. Thus the saccharide compositions can be freely used in compositions such as food products, tobaccos, cigarettes, feeds, pet foods, cosmetics, pharmaceuticals, shaped products, and others such as daily products, agricultural and fishery products, chemical reagents, and products for chemical industries.

The present saccharide compositions containing fructosyl-transferred saccharides can be used intact as a seasoning for sweetening. If necessary, the compositions can be used together with adequate amounts of one or more other sweeteners, for example, powdered syrup, glucose, maltose, trehalose, sucrose, isomerized sugar, honey, maple sugar, sorbitol, maltitol, lactitol, dihydrochalcone, stevioside, α-glycosyl stevioside, rebaudioside, glycyrrhizin, L-aspartyl L-phenylalanine methyl ester, saccharin, glycine, and alanine, and/or a filler such as dextrin, starch and lactose.

Because the present saccharide compositions have a taste that well harmonizes with other substances having sourness, acid, saltiness, bitterness, astringency, and deliciousness, they can be freely used in food products in general as a sweetener, taste-improving agent, and quality-improving agent.

The present saccharide compositions can be used as a seasoning for soy sauce, powdered soy sauce, "miso", "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "takuan-zuke-no-moto" (an instant mix for Japanese radish), "hakusai-zuke-no-moto" (an instant mix for Chinese cabbage), "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar.

The present saccharide compositions can be also used to sweeten and improve the taste and property of "wagashi" (Japanese cakes) such as "senbei" (a rice cracker), "arare-mochi" (a rice-cake cube), "okoshi" (a millet-and-rice cake), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castella and "amedama" (a Japanese toffee); confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as "kajitsu-no-syrup-zuke" (a preserved fruit) and "korimitsu" (a sugar syrup for shaved ice); pastes such as flour paste, peanut paste, fruit paste and spread; processed fruits and vegetables such as jam, marmalade, "syrup-zuke" (fruit pickles) and "toka" (conserves); pickles and pickled products such as "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); meat products such as ham and sausage; products of fish meat such as fish ham, fish sausage, "kamaboko" (a steamed fish paste), "chikuwa" (a kind of fish paste) and "tenpura" (a Japanese deep-fat fried fish paste); "chinmi" (relish) such as "uni-no-shiokara" (salted guts of sea urchin), "ika-no-shiokara" (salted guts of squid), "su-konbu" (processed tangle), "saki-surume" (dried squid strips) and "fugu-no-mirin-boshi" (a dried mirin-seasoned swellfish); "tsukudani" (foods boiled down in soy sauce) such as those of laver, edible wild plants, dried squid, fish and shellfish; daily dishes such as "nimame" (cooked beans), potato salad and "konbu-maki" (a tangle roll); milk products; canned and bottled products such as those of meat, fish meat, fruit and vegetable; alcoholic beverages such as sake, synthetic sake, wine, and liquors; soft drinks such as coffee, tea, cocoa, juice, carbonated beverage, sour milk beverage and beverage containing lactic acid bacteria; instant food products such as instant pudding mix, instant hot cake mix and "sokuseki-shiruko" (an instant mix of adzuki-bean soup with rice cake) and instant soup mix; and beverages such as baby foods, foods for therapy, beverages supplemented with nutrition, peptide foods and frozen foods; as well as for improving the tastes and qualities of the aforementioned food products.

The present saccharide compositions can be further used in feeds and pet foods for animals such as domestic animals, poultry, and fishes to improve their taste preferences and improve the growth of the animals. These compositions can be arbitrary used as a sweetener, taste-improving agent, masking agent, and quality-improving agent in other products in a paste or liquid form such as a tobacco, cigarette, dentifrice, lipstick, rouge, chapped lip, internal medicine, tablet, troche, cod liver oil in a drop form, cachou, oral refrigerant, gargle, cosmetic, and pharmaceutical.

The present saccharide compositions can be used as a quality-improving agent and a stabilizer for solutions of biologically active substances which are susceptible to lose their effective ingredients and activities, as well as in health foods and pharmaceuticals containing the biologically active substances. Examples of these biologically active substance are lymphokines such as α-, β- and γ-interferons, tumor necrosis factor-α (TNF-α), tumor necrosis factor-β (TNF-β), macrophage migration inhibitory factor, colony-stimulating factor, transfer factor and interleukin 2; hormones such as insulin, growth hormone, prolactin, erythropoietin, follicle-stimulating hormone, and placental hormone; biological preparations such as BCG vaccine, Japanese encephalitis vaccine, measles vaccine, live polio vaccine, smallpox vaccine, tetanus toxoid, habu venom or Trimeresurus antitoxin, and human immunoglobulin; antibiotics such as penicillin, erythromycin, chloramphenicol, tetracycline, streptomycin, and kanamycin sulfate; vitamins such as thiamine, riboflavin, L-ascorbic acid, cod liver oil, carotenoid, ergosterol, and tocopherol; enzymes such as lipase, elastase, urokinase, protease, β-amylase, isoamylase, glucanase, and lactase; extracts such as ginseng extract, snapping turtle extract, chlorella extract, aloe extract, and propolis extract; viable micro-organisms such as viruses, lactic acid bacteria, and yeasts; and other biologically active substances such as royal jelly. By using the present non-reducing saccharides, relatively-low reducing saccharides containing them, and trehalose prepared from these saccharides, the aforementioned biologically active substances are arbitrarily prepared into health foods and pharmaceuticals with a satisfactorily-high stability and quality without fear of losing or inactivating their effective ingredients and activities.

As is described above, the compositions as referred to in the present invention include orally or parenterally administrable food products and pharmaceuticals and can be used in cosmetics, daily products, chemical reagents, chemical industries, and products in agriculture, forestry, and fisheries.

The methods to incorporate the present saccharide compositions containing fructosyl-transferred saccharides into the above compositions include conventional methods, for example, mixing, kneading, dissolving, melting, soaking, permeating, sprinkling, applying, coating, spraying, injecting, crystallizing, and solidifying. The present saccharide compositions are generally incorporated into these compositions in an amount of 0.1% or more, preferably, 0.5% or more with respect to the fructosyl-transferred saccharides, d.s.b.

The following experiments explain the present invention in more detail:

EXPERIMENT 1
Production of enzyme

In 500-ml Erlenmeyer flasks were placed 100 ml aliquots of a liquid nutrient culture medium which consists of 1.0 w/v % sucrose, 0.5 w/v % polypeptone, 0.1 w/v % yeast extract, 0.1 w/v % potassium dihydrogenphosphate, 0.06 w/v % disodium hydrogenphosphate dihydrate, 0.05 w/v % magnesium sulfate heptahydrate, 0.3 w/v % calcium carbonate, and water. The flasks were sterilized by autoclaving at 121° C. for 15 min and cooled, then inoculated with a stock culture of Bacillus sp. V230 (FERM BP-5054), and incubated at 30° C. for 20 hours under rotary shaking conditions of 200 rpm. The cultures were pooled and used as a seed culture.

About 7 L of a fresh preparation of the same nutrient culture medium was placed in a 10-L fermenter, sterilized by heating, and cooled to 30° C., then inoculated with one v/v % of the above seed culture, followed by the incubation at 30° C. for about 20 hours under agitation-aeration conditions.

An about 6.5 L of the resulting culture was centrifuged at 15,000×g for 20 min to obtain an about 6.3 L culture supernatant with an activity of 3.6 units/ml of β-fructofuranosidase.

EXPERIMENT 2
Purification of enzyme

Ammonium sulfate was added to and dissolved in the culture supernatant in Experiment 1 to give a saturation degree of 0.8, and the solution was allowed to stand at 4° C. overnight, then centrifuged to collect a precipitate.

The precipitate was dissolved in 10 mM acetate buffer (pH 6.0) containing 5 mM calcium chloride, and the solution was dialyzed against the same buffer for a day, followed by centrifugation at 15,000×g for 20 min to remove insoluble substances. The supernatant (210 ml) was subjected to ion-exchange column chromatography using 380 ml of "DEAE-TOYOPEARL®650", a gel commercialized by Tosoh Corporation, Tokyo, Japan.

The present β-fructofuranosidase adsorbed on the gel was eluted with 0.1M salt solution, and the eluted fractions were pooled and purified by the following procedures: Dialyze the solution against a fresh preparation of the same buffer containing one M ammonium sulfate, and the dialyzed inner solution was centrifuged at 15,000×g for 20 min to remove insoluble substances. The supernatant was subjected to hydrophobic column chromatography using 100 ml "BUTYL-TOYOPEARL®", a gel commercialized by Tosoh Corporation, Tokyo, Japan. The β-fructofuranosidase adsorbed on the gel was eluted from the column with a linear gradient solution of ammonium sulfate decreasing from 1M to 0M, followed by collecting fractions with the enzyme activity.

The fractions were pooled and subjected to ion-exchange column chromatography using 10 ml "DEAE-TOYOPEARL® 650", followed by collecting the eluted fractions with the enzyme activity.

The yield of the enzyme preparation thus obtained was about 13% with respect the total activity in the culture supernatant. The specific activity of the enzyme preparation was 205 units/mg protein. The protein content was assayed on the Lowry method using calf serum albumin as a standard protein.

The purity of the purified β-fructofuranosidase was assayed on gel electrophoresis in a 7.5 w/v % polyacrylamide gel, resulting in a single protein band with a relatively high purity.

EXPERIMENT 3
Property of enzyme

A β-fructofuranosidase preparation obtained by the method in Experiment 2 was electrophoresed in a 10 w/v % sodium dodecyl sulfate polyacrylamide (SDS) gel using marker proteins commercialized by Japan Bio-Rad Laboratories, Tokyo, Japan, then compared with the molecular weights of marker proteins revealing that the enzyme has a molecular weight of 49,000±5,000 daltons. When assayed on gel filtration using a column of "TSKgel G3000SW", 7.8 mm in diameter and 300 mm long, commercialized by Tosoh Corporation, Tokyo, Japan, the enzyme showed a molecular weight of 37,000±3,000 daltons.

The purified β-fructofuranosidase was isoelectrophoresed in a 2 w/v % "AMPHOLINE" gel, a polyacrylamide gel for isoelectrophoresis commercialized by Pharmacia LKB Biotechnology AB, Uppsala, Sweden, followed by coloring the proteins in the gel and measuring the gel pH to check the pH of the enzyme revealing that the pI was 4.6±0.5.

Figure 2:
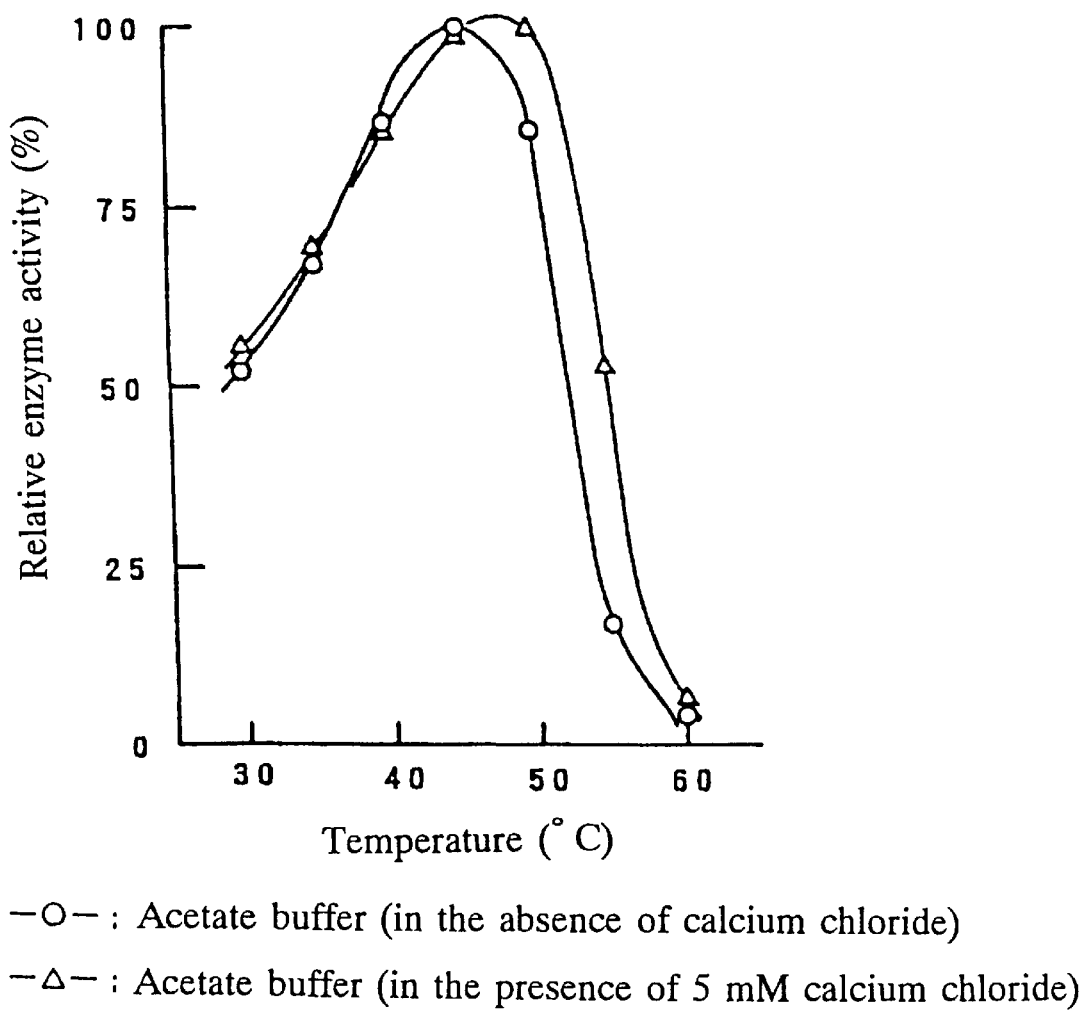
FIG. 2 shows the influence of temperature on the activity of the present β-fructofuranosidase.
Figure 3:
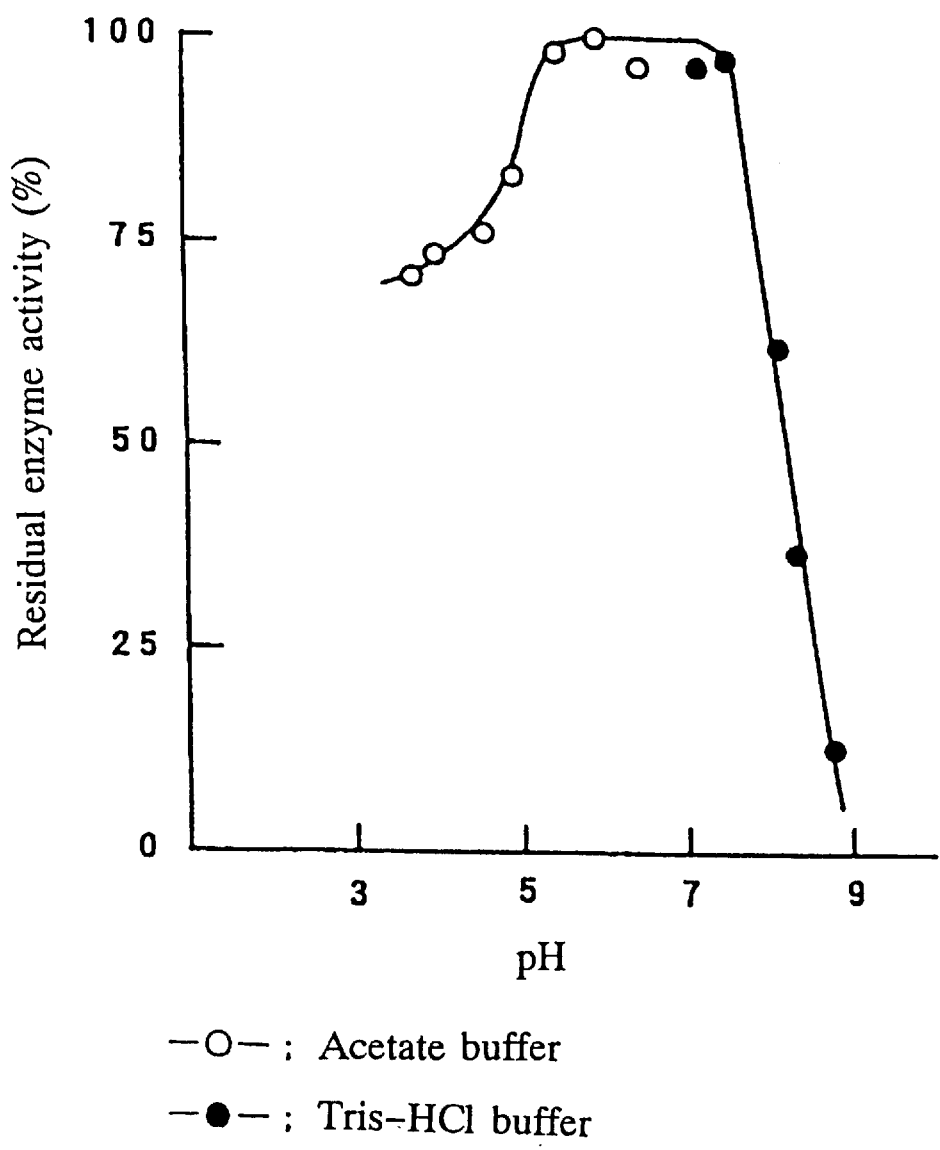
FIG. 3 shows the pH stability of the present β-fructofuranosidase.
Figure 4:
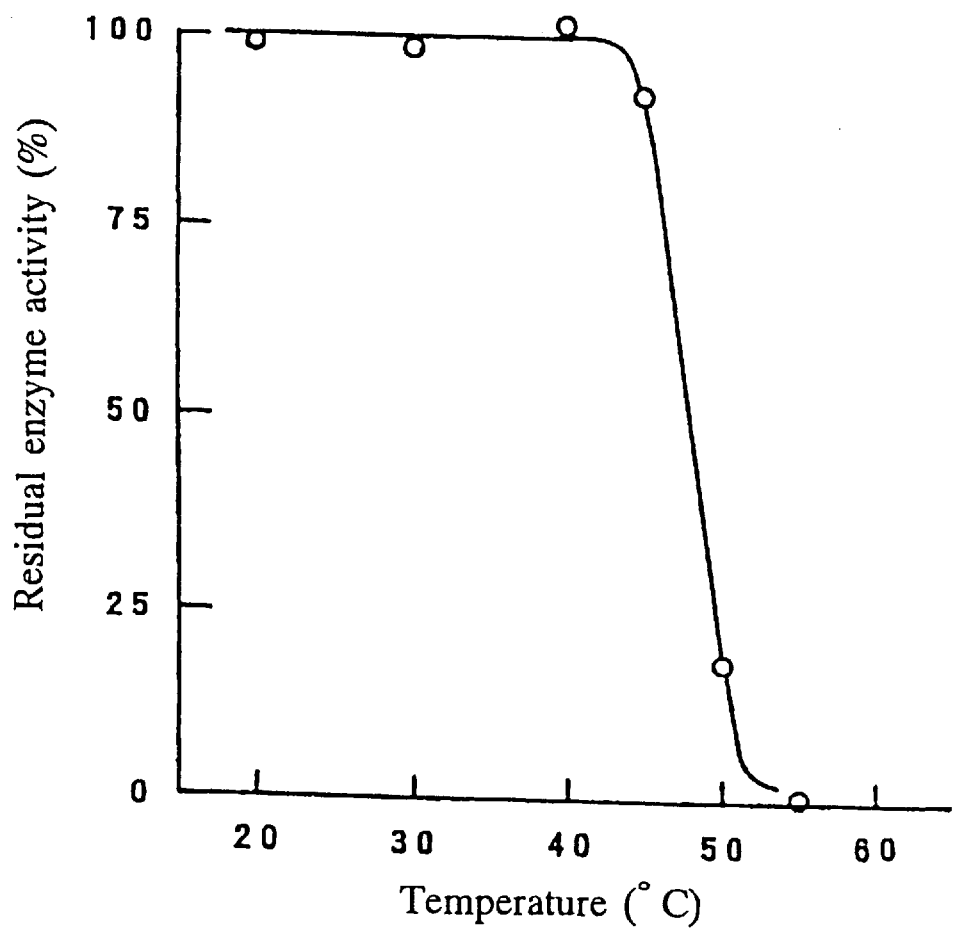
FIG. 4 shows the thermal stability of the present β-fructofuranosidase.

In accordance with the method used in the above assay for the enzyme activity, the influence of pH and temperature on the present β-fructofuranosidase activity was studied in the presence of or in the absence of 5 mM calcium chloride. These results on pH and temperature were respectively in FIGS. 1 and 2. The optimum pH of the enzyme was about 5.5–6.0 when incubated at 40° C. for 10 min both in the presence of and in the absence of calcium ion, while the optimum temperature of the enzyme was about 50° C. in the presence of calcium ion and about 45° C. in the absence of calcium ion when incubated at pH 6.0 for 10 min. The pH stability of the present enzyme was determined by incubating in 50 mM buffers with different pHs at 4° C. for 24 hours, and assaying the residual enzyme activity after adjusting the buffers to pH 6. The thermal stability of the enzyme was determined by incubating in 20 mM acetate buffers (pH 6.0) at different temperatures for an hour, and assaying the residual enzyme activity in each buffer after cooling the buffers. The results of pH and thermal stabilities of the present enzyme were respectively in FIGS. 3 and 4. The pH stability of the enzyme was about 5.0–8.0, and the thermal stability was about 45° C. The presence of calcium ion did not influence the pH and thermal stabilities. One mM $Cu^{++}$, $Pb^{++}$, $Fe^{++}$, $Fe^{+++}$ or $Hg^{++}$ inhibited the enzyme activity.

EXPERIMENT 4
Substrate specificity

A solution with a final concentration of 2 w/v % raffinose, erlose, stachyose, lactose, xylofructoside, maltose, cellobiose, lactose, inulin or laevan as a substrate was mixed with 2 units/g substrate of a β-fructofuranosidase obtained by the method in Experiment 2, and allowed to react enzymatically at 40° C. and pH 5.5 for 24 hours. The reaction mixture was subjected to thin layer chromatography (hereinafter abbreviated as "TLC") using "KIESEL GEL 60", an aluminum plate, 20×20 cm, commercialized by Merck & Co., Inc., New Jersey, U.S.A., to confirm whether the enzyme acts on these saccharides. The solvent system used in the TLC consisted of 1-butanol, pyridine, and water (=7:3:1 by volume), and samples were developed once at ambient temperature. The saccharides comprising fructose units as constituent saccharides were colored by spraying a 0.5-N phosphoric acid solution containing 0.2 w/v % naphthoresorcinol and heating at 110° C. for about 5 min, while other saccharides were colored by spraying a methanol solution containing 20 w/v % sulfuric acid and heating at 110° C. for about 10 min.

As a result, it was found that the present β-fructofuranosidase acts on sucrose, raffinose, erlose, stachyose, lactosucrose, and xylofructoside to release fructose specifically, but does not act on maltose, cellobiose, lactose, inulin and laevan.

EXPERIMENT 5
Acceptor specificity

A saccharide solution with a final concentration of 10%, which consists of one of the monosaccharides, oligosaccharides, and alcohols in Table 1, and an equal amount of sucrose as a donor, d.s.b., was mixed with 2 units/g sucrose of a purified β-fructofuranosidase obtained by the method in Experiment 2, and allowed to react enzymatically at 40° C. and pH 5.5 for 24 hours. The mixtures before the enzymatic reaction and the reaction mixtures after the enzymatic reaction were subjected to TLC similarly as in Experiment 4, and the saccharides were colored by spraying 0.5-N phosphoric acid containing 0.2 w/v % naphthoresorcinol and heating at 110° C. for about 5 min to check the formation of transferred saccharides. The results were in Table 1:

TABLE 1

| Acceptor | Transferred saccharide | Acceptor | Transferred saccharide |
| --- | --- | --- | --- |
| D-Xylose | ++ | Turanose | + |
| D-Galactose | ++ | Palatinose | + |
| D-Mannose | + | Melibiose | ++ |
| D-Fructose | + | Raffinose | + |
| D-Sorbose | + | D-Xylitol | ++ |
| D-Arabinose | + | D-Sorbitol | ++ |
| D-Rhamnose | + | Maltitol | ++ |
| Maltose | ++ | Glycerol | ++ |
| Isomaltose | ++ | Methanol | + |
| Kojibiose | + | Ethanol | + |
| Trehalose | ++ | Ethylene glycol | ++ |
| Neotrehalose | + | 1-Butanol | – |
| Cellobiose | ++ | 2-Butanol | – |
| Maltotriose | ++ | 1-Propanol | – |
| Panose | ++ | 2-Propanol | – |
| Lactose | ++ | | |

Note:
The transferred saccharide formation was judged by comparing with an enzymatic reaction mixture using sucrose only. The symbols "–", "+" and "++" mean "unchanged", "the spot for acceptor was slightly reduced while forming a fructosyl-transferred saccharide in small quantities", and "the spot for acceptor was significantly reduced while forming a fructosyl-transferred saccharide in large quantities".

As is shown in Table 1, it was revealed that the present β-fructofuranosidase effectively transfers fructosyl residue to reducing saccharides such as D-xylose, D-galactose, maltose, isomaltose, cellobiose, maltotriose, panose, lactose, and melibiose, as well as non-reducing saccharides such as trehalose. It was also found that the enzyme effectively transfers a fructosyl residue to sugar alcohols such as D-xylitol, D-sorbitol, and maltitol, as well as alcohols such as glycerol and ethylene glycol, to produce fructosyl-transferred saccharides.

EXPERIMENT 6
Fructosyl-transferred saccharide from sucrose and reducing saccharide A confirmation test was conducted to identify the fructosyl-transferred saccharides, formed by the saccharide-transferring reaction using the present β-fructofuranosidase. A part of the reaction mixture obtained in Experiment 5 using sucrose and lactose as substrates was diluted with 20 mM acetate buffer (pH 4.5) to give a saccharide concentration of 2%, and 0.5 ml of the diluted solution was mixed with 0.1 unit of invertase or 0.1 unit of β-galactosidase, both of which are commercialized by Seikagaku-Kogyo Co., Ltd., Hyogo, Japan, followed by the enzymatic reaction at 40° C. for 20 hours. The reaction mixture obtained by using the present β-fructofuranosidase and other reaction mixtures obtained by treating the reaction mixture with invertase or β-galactosidase were analyzed for saccharide components on gas chromatography (GLC). A part of each reaction mixture was dried, dissolved in pyridine, and trimethylsilated to prepare a sample for GLC analysis. The conditions and equipment used in the analysis were as follows: GCL column, a stainless steel column, 3 mm in diameter and 2 m long, packed with 2% "SILICONE OV-17/ CHROMOSOLVE W" commercialized by GL Sciences Inc., Tokyo, Japan; carrier gas, nitrogen gas, a flow rate of 40 ml/min; Column oven temperature, 160–320° C., a temperature increasing rate of 7.5° C./min; and detector, hydrogen flame ionization detector.

As a result, it was found that the retention time of a peak for a fructosyl-transferred saccharide formed from sucrose and lactose by the action of the present β-fructofuranosidase coincided with that of the authentic lactosucrose or lactosylfructoside. It was also found that the peak of the fructosyl-transferred saccharide was not detected when treated with invertase or β-galactosidase because the saccharide was decomposed into fructose and lactose by the action of invertase or into galactose and sucrose by the action of β-galactosidase. Considering the reaction dynamics of invertase and β-galactosidase, it was concluded that the fructosyl-transferred saccharide is lactosucrose.

Based on the data from GLC analyses on reaction mixtures before and after the invertase treatment and on authentic saccharides, the fructosyl-transferred saccharides formed from xylose, maltose, and isomaltose as acceptors were identified as xylosylfructoside, erlose (maltosylfructoside), and isomaltosylfructoside, respectively. The fructosyl-transferred saccharides, formed from these reducing saccharides as acceptors by the action of the present β-fructofuranosidase, are judged to have β-fructofuranosidic linkages at C-1 of the reducing saccharide residues.

EXPERIMENT 7
Fructosyltrehalose

Fructosyltrehalose was isolated and studied on structure to identify the saccharide that transferred to trehalose. A saccharide solution containing sucrose and trehalose in respective amounts of 20% was adjusted to pH 6.0, mixed with 4 units/g sucrose of a purified β-fructofuranosidase obtained by the method in Experiment 2, allowed to react enzymatically at 55° C. for 20 hours, and heated at 100° C. for 10 min to inactivate the remaining enzyme. The reaction mixture containing about 23% fructosyltrehalose, d.s.b., was purified on decolorization with an activated charcoal, filtration, and desalting with ion exchangers in H- and OH-form, concentrated up to about 50%, and subjected to column chromatography, followed by collecting fractions rich in fructosyltrehalose.

The resin used for the fractionation was "XT-1016 (Na-form, polymerization degree of 4%)", a strong-acid cation exchanger commercialized by Tokyo Organic Chemical Industries, Ltd., Tokyo, Japan. In use, it was first suspended in water, then packaged in 2 jacketed-stainless steel columns, 3 cm in diameter and 1 m long each, cascaded in series to give a total gel-bed depth of about 2 m. The fractionation procedures were as follows: Feed a saccharide solution to the columns in an amount of 5 v/v % with respect to the resin while keeping the inner column temperature to 40° C., then fractionate the solution by feeding water heated to 40° C. at SV (space velocity) 0.15 to collect fractions rich in fructosyltrehalose. Pool the fractions, desalt the mixture solution, purify the desalted solution, and concentrate the purified the solution into an about 40% solution. Feed the concentrate to a column packed with "YMC-PACK ODS", a column of octadecylsilica gel commercialized by YMC Co., Ltd., Tokyo Japan, to collect fractions rich in fructosyltrehalose. Pool the solutions which were obtained by repeating these procedures, desalt the mixture solution, purify the desalted solution, concentrate the purified solution, and dry the concentrate in vacuo to obtain a powder rich in fructosyltrehalose in a yield of about 10%, d.s.b. The powder contained about 98% fructosyltrehalose, d.s.b.

Using the powder the structure of fructosyltrehalose was analyzed by an enzymatic method and GLC analysis for partial methylhexitolacetates. As a result, it was found that the invertase treatment decomposed the fructosyltrehalose, formed by the action of the present β-fructofuranosidase, into fructose and trehalose moieties in a molar ratio of 1:1. The GLC analysis on partial methylhexitolacetates, which were obtained by methylating the fructosyltrehalose, hydrolyzing the methylated products with acids, reducing the hydrolyzed products, and acetylating the reduced products, detected 1,5,6-tri-O-acetyl-2,3,4-tri-O-methylglucitol and 1,5-di-0-acetyl-2,3,4,6-tetra-O-methylglucitol in an equimolar ratio. These results revealed that the fructosyltrehalose is identified as a trisaccharide where trehalose binds to fructosyl residue via the β-2,6 linkage.

EXPERIMENT 8

Acute toxicity test

Using 7-week-old dd-strain mice, a powder rich in lactosucrose, obtained by the method in Example A-4 described later, was administered orally to the mice for acute toxicity test. No mouse died up to a dose of 15 g/kg mouse, and a higher dose test was impossible. Thus, the lactosucrose is relatively low in toxicity. Similarly as above, a powder rich in erlose obtained by the method in Example A-6 described later, a syrup rich in xylosylfructoside obtained by the method in Example A-8 described later, a syrup rich in fructosyltrehalose obtained by the method in Example A-11, or a syrup rich in isomaltosyl-fructoside obtained by the method in Example A-12 described later was orally administered to 7-week-old dd-strain mice for acute toxicity test. No mouse died up to a dose of 15 g/kg mouse, and a higher does test was impossible. Based on these results, these saccharides were relatively low in toxicity.

The following Examples A and B illustrate the present β-fructofuranosidase and the method for producing saccharide compositions containing fructosyl-transferred saccharides:

EXAMPLE A-1

A seed culture of Bacillus sp. V230 (FERM BP-5054) was inoculated in a nutrient culture medium and cultured for about 24 hours under aeration-agitation conditions similarly as in Experiment 1 except for using a 30-L fermenter and an about 20 L of a nutrient culture medium containing 2 w/v % sucrose as the culture medium. The β-fructofuranosidase activity in the culture supernatant was 7.3 units/ml. The culture was filtered with an MF membrane, and the filtrate was concentrated with a UF membrane to obtain an enzyme solution with an about 130 units/ml of β-fructofuranosidase activity in a yield of about 80% with respect to the total enzyme activity of the culture.

EXAMPLE A-2

An aqueous solution containing sucrose and lactose in respective amounts of 20% was adjusted to pH 5.5, mixed with one unit/g sucrose of β-fructofuranosidase obtained by the method in Example A-1, and allowed to react enzymatically at 55° C. for 16 hours. The reaction mixture was heated at 90° C. for 30 min to inactivate the remaining enzyme, cooled, and, in a conventional manner, decolored with an activated charcoal, filtered, purified by desalting with ion exchangers in H- and OH-form, and concentrated to obtain a syrup with a concentration of about 75% in a yield of about 95%, d.s.b.

Because the syrup contains about 37% lactosucrose, d.s.b., and has a pleasant taste and sweetness and an adequate viscosity and humectancy, it can be arbitrarily used in food products, cosmetics, and pharmaceuticals as a sweetener, taste-improving agent, filler-imparting agent, growth-promoting agent for bifid bacteria, and mineral absorption-promoting agent.

EXAMPLE A-3

An aqueous solution containing 22% sucrose and 18% lactose was adjusted to pH 6.0, mixed with one unit/g sucrose of the β-fructofuranosidase in Example A-1 and 5% wet invertase-defective yeasts with respect to the contents, d.s.b., and allowed to react enzymatically at 35° C. for 20 hours while keeping the pH of the mixture to 6–7 by the addition of 1-N sodium hydroxide. The reaction mixture was heated at 90° C. for 30 min to inactivate the remaining enzyme, cooled, and, in a conventional manner, decolored with an activated charcoal, filtered, purified by desalting with ion exchangers in H- and OH-form, and concentrated into an about 75% syrup in a yield of about 70%, d.s.b.

The product contains about 65% lactosucrose, d.s.b., and has a pleasant taste and sweetness and an adequate viscosity and humectancy, so that it can be arbitrarily used in compositions such as food products, cosmetics, and pharmaceuticals as a sweetener, taste-improving agent, stabilizer, growth-promoting agent for bifid bacteria, and mineral absorption-promoting agent.

EXAMPLE A-4

A solution containing about 37% lactosucrose as a material saccharide solution, obtained by the method in Example A-2, was concentrated into an about 45% solution. To increase the lactosucrose content, the concentrated solution was subjected to column chromatography using "XT-1016 (Na-form, polymerization degree of 4%)", a strong-acid cation exchange resin commercialized by Tokyo Organic Chemical Industries, Ltd., Tokyo, Japan. The procedures were as follows: The resin was packed in 4 jacketed-stainless steel columns, an inner diameter of 5.4 cm, cascaded in series to give a total gel-bed depth of 20 m. Five v/v % of the concentrated solution was fed to the columns while keeping the inner column temperature to 40° C., and fractionated by feeding to the column water heated to 40° C. at SV 0.2 to obtain fractions rich in lactosucrose. The fractions were pooled, purified, concentrated, dried in vacuo, and pulverized to obtain a powder rich in lactosucrose in a yield of about 30%, d.s.b.

Because the product contains about 90% lactosucrose, d.s.b., and has a relatively-low reducibility and cariogenicity, as well as a pleasant taste and sweetness and a satisfactory humectancy, it can be arbitrarily used in compositions such as food products, cosmetics, and pharmaceuticals as a sweetener, taste-improving agent, stabilizer, filler-imparting agent, growth-promoting agent for bifid bacteria, and mineral absorption-promoting agent.

EXAMPLE A-5

A saccharide solution containing sucrose and maltose in respective amounts of 20% was adjusted to pH 5.5, mixed with one unit/g sucrose of β-fructofuranosidase obtained by the method in Example A-1, and allowed to react enzymatically at 50° C. for 24 hours. The reaction mixture was heated at 9° C. for 30 min to inactivate the remaining enzyme, cooled, and, in a conventional manner, decolored with an activated charcoal, filtered, purified by desalting with ion exchangers in H- and OH-form, and purified to obtain an about 75% syrup in a yield of about 95%, d.s.b.

Because the product contains about 28% erlose, d.s.b., and has a satisfactory taste and sweetness and an adequate viscosity and humectancy, it can be arbitrarily used in food products, cosmetics and pharmaceuticals.

EXAMPLE A-6

A solution containing about 28% erlose as a material saccharide solution, obtained by the method in Example A-5, was concentrated into an about 45% solution. To increase the erlose content, the concentrated solution was column chromatographed according to the method in Example A-4 except that "DOWEX 50WX4 (Ca-form)" as the ion exchanger commercialized by Dow Chemical Company, Midland, Mich., U.S.A., followed by collecting fractions rich in erlose. The fractions were pooled, purified, concentrated, dried in vacuo, and pulverized to obtain a powder rich in erlose in a yield of about 25%, d.s.b.

Because the product contains about 84% erlose, d.s.b., and has a relatively-low reducibility and cariogenicity, as well as a pleasant taste and sweetness and a satisfactory humectancy, it can be arbitrarily used in compositions such as food products, cosmetics and pharmaceuticals.

EXAMPLE A-7

A saccharide solution containing 30% sucrose and 15% xylose was adjusted to pH 5.5, mixed with 0.5 unit/g sucrose of β-fructofuranosidase obtained by the method in Example A-1, and allowed to react enzymatically at 50° C. for 40 hours. The reaction mixture was heated at 90° C. for 30 min to inactivate the remaining enzyme, cooled, and, in a conventional manner, decolored with an activated charcoal, filtered, purified by desalting with ion exchangers in H- and OH-form, and further purified to obtain an about 75% syrup in a yield of about 95%, d.s.b.

Because the product contains about 35% xylosylfructoside, d.s.b., and has a pleasant taste and sweetness, an adequate viscosity and humectancy, and a relatively low cariogenicity, it can be arbitrarily used in compositions such as food products, cosmetics, and pharmaceuticals as a sweetener, taste-improving agent, stabilizer, growth-promoting agent for bifid bacteria, and mineral absorption-promoting agent.

EXAMPLE A-8

A saccharide solution containing 30% sucrose and 15% xylose was adjusted to pH 6.0, mixed with 0.5 unit/g sucrose of β-fructofuranosidase obtained by the method in Example A-1, and allowed to react enzymatically at 50° C. for 40 hours. The reaction mixture was heated at 100° C. while keeping the pH to 10 or more by the addition of sodium hydroxide, cooled, and, in a conventional manner, decolored with an activated charcoal, filtered, purified by desalting with ion exchangers in H- and OH-form, and concentrated to obtain an about 75% syrup in a yield of about 55%, d.s.b.

Because the product contains about 60% xylosylfructoside, d.s.b., and has a pleasant taste and sweetness and an adequate viscosity and humectancy, it can be arbitrarily used in compositions such as food products, cosmetics, and pharmaceuticals as a sweetener, taste-improving agent, stabilizer, growth-promoting agent for bifid bacteria, and mineral-absorption-promoting agent.

EXAMPLE A-9

A saccharide solution containing sucrose and trehalose in respective amounts of 20% was adjusted to pH 5.5, mixed with 4 units/g sucrose of β-fructofuranosidase obtained by the method in Example A-1, and allowed to react enzymatically at 55° C. for 16 hours. The reaction mixture was heated at 90° C. for 30 min to inactivate the remaining enzyme, cooled, and, in a conventional manner, decolored with an activated charcoal, filtered, purified by desalting with ion exchangers in H- and OH-form, and concentrated to obtain an about 75% syrup in a yield of about 95%, d.s.b.

Because the product contains about 24% fructosyltrehalose, d.s.b., and has a pleasant taste and sweetness, an adequate viscosity and humectancy, and a relatively low cariogenicity, it can be arbitrarily used in compositions such as food products, cosmetics, and pharmaceuticals as a sweetener, taste-improving agent, stabilizer, growth-promoting agent for bifid bacteria, and mineral-absorption-promoting agent.

EXAMPLE A-10

A saccharide solution containing sucrose and trehalose in respective amounts of 20%, d.s.b., was adjusted to pH 5.5, mixed with 4 units/g sucrose of the β-fructofuranosidase in Example A-1 and 5% wet invertase-defective yeasts with respect to the contents, d.s.b., and allowed to react enzymatically at 35° C. for 20 hours while keeping the pH to 6–7 by the addition of 1-N sodium hydroxide. The reaction mixture was heated at 90° C. for 30 min to inactivate the remaining enzyme, cooled, and, in a conventional manner, decolored with an activated charcoal, filtered, purified by desalting with ion exchangers in H- and OH-form, and concentrated into an about 75% syrup in a yield of about 70%, d.s.b.

The product contains about 34% fructosyltrehalose, d.s.b., and has a pleasant taste and sweetness and an adequate viscosity and humectancy. Thus it can be arbitrarily used in compositions such as food products, cosmetics, and pharmaceuticals as a sweetener, taste-improving agent, stabilizer, growth-promoting agent for bifid bacteria, and mineral absorption-promoting agent.

EXAMPLE A-11

An aqueous solution as a material saccharide solution containing about 24% fructosyltrehalose, d.s.b., obtained by the method in Example A-9, was concentrated into an about 45% solution. To increase the fructosyltrehalose content, the concentrated solution was column chromatographed according to the method in Example A-4 except that "DOWEX 50WX4 (Ca-form)" was used as the resin for fractionation, followed by collecting fractions rich in fructosyltrehalose. The fractions were pooled, purified, concentrated, dried in vacuo, and pulverized to obtain a powder rich in fructosyltrehalose in a yield of about 20%, d.s.b.

Because the product contains about 80% fructosyltrehalose, d.s.b., and has a pleasant taste and sweetness and an adequate viscosity and humectancy, it can be arbitrarily used in compositions such as food products, cosmetics, and pharmaceuticals as a sweetener, taste-improving agent, stabilizer, filler-imparting agent, growth-promoting agent for bifid bacteria, and mineral absorption-promoting agent.

EXAMPLE 12

A saccharide solution containing 30% sucrose and 15% isomaltose, d.s.b., was adjusted to pH 5.5, mixed with 0.5 unit/g sucrose of β-fructofuranosidase obtained by the method in Example A-1, and allowed to react enzymatically at 50° C. for 40 hours. The reaction mixture was heated at 90° C. for 30 min to inactivate the remaining enzyme, cooled, and, in a conventional manner, decolored with an activated charcoal, filtered, purified by desalting with ion exchangers in H- and OH-form, and concentrated to obtain an about 75% syrup in a yield of about 95%, d.s.b.

Because the product contains about 25% isomaltosylfructoside, d.s.b., and has a pleasant taste and sweetness, an adequate viscosity and humectancy, and a relatively low cariogenicity, it can be arbitrarily used in compositions such as food products, cosmetics, and pharmaceuticals as a sweetener, taste-improving agent, stabilizer, growth-promoting agent for bifid bacteria, and mineral-absorption-promoting agent.

EXAMPLE B-1

Mixed sweetener

One part by weight of a powder rich in lactosucrose obtained by the method in Example A-4 was mixed to homogeneity with 0.05 part by weight of "α-G SWEET", α-glycosylstevioside commercialized by Toyo Sugar Refining Co., Ltd., Tokyo, Japan, to obtain a powdery sweetener. The product has a high-quality sweetness and an about 2-fold higher sweetening power of sucrose. The product exerts a satisfactory growth-promoting activity for bifid bacteria and can be selectively used in the maintenance and promotion of health and beauty, the prevention of geriatric diseases, the promotion of recovery of health during and after diseases, and the treatment and/or the prevention of hyperammonemia, and hepatic encephalopathy. The product can be also used in the prevention of infectious diseases, the prevention of diarrhea, the promotion of appetite, the promotion of growth, and the inhibition of unsatisfactory feces' smell of domestic animals and poultry.

EXAMPLE B-2

Hard candy

Thirty parts by weight of a syrup containing isomaltosylfructoside, obtained by the method in Example A-12, was dissolved in 80 parts by weight of a hydrogenated maltose syrup with a moisture content of 25%, and the solution was concentrated in vacuo up to give a moisture content of less than 2%. The concentrate was mixed with one part by weight of citric acid and adequate amounts of a lemon flavor and a coloring agent, and the mixture was shaped in a conventional manner into a hard candy.

The product has a high-quality sweetness and a less cariogenicity. Because the product exerts a growth-promoting activity for bifid bacteria and a mineral absorption-promoting activity, it can be arbitrarily used in the maintenance and promotion of health and beauty, the prevention of geriatric diseases, the promotion of recovery of health during and after diseases, and the treatment and/or the prevention of diseases.

EXAMPLE B-3

Chewing gum

Two parts by weight of a gum base was heated until it softened and mixed with 4 parts by weight of a powder rich in lactosucrose obtained by the method in Example A-4, 3 parts by weight of glucose, and adequate amounts of a mint flavor and a coloring agent. The mixture was kneaded by a roll in a conventional manner and shaped to obtain a chewing gum.

The product has a satisfactory texture and sweetness, exerts a growth-promoting activity for bifid bacteria, and can be arbitrarily used in the maintenance and promotion of health and beauty, the prevention of geriatric diseases, the promotion of recovery of health during and after diseases, and the treatment and/or the prevention of diseases.

EXAMPLE B-4

Chocolate

Forty parts by weight of cacao paste, 10 parts by weight of cacao butter, 15 parts by weight of a powder rich in erlose obtained by the method in Example A-6, 10 parts by weight of sucrose, and 15 parts by weight of milk powder were mixed, then passed through a refiner. After decreasing the particle size, the mixture was placed in a conche and mixed with 0.5 part by weight of lecithin, followed by kneading up at 50° C. for 2 days. The kneaded mixture was poured into a molding machine for shaping and solidified.

The product, which is substantially free from fat and sugar blooms, has a satisfactory taste and melting property on the tongue.

EXAMPLE B-5

Milk beverage

Seventy parts by weight of a coffee extract, 100 parts by weight of milk, 24 parts by weight of a syrup rich in lactosucrose obtained by the method in Example A-3, and adequate amounts of a coffee flavor and a coloring agent were mixed to homogeneity, and, in a conventional manner, sterilized, cooled, injected, and packed to obtain a milk beverage.

The product is a coffee blended milk with a pleasant flavor and taste. Because the product exerts a growth-promoting activity for bifid bacteria and a mineral absorption-promoting activity, it can be arbitrarily used in the maintenance and promotion of health and beauty, the prevention of geriatric diseases, and the promotion of recovery of health during and after diseases.

EXAMPLE B-6

Custard cream

Five hundred parts by weight of corn starch, 400 parts by weight of "SUNMALT®", a maltose product commercialized by Hayashibara Shoji, Inc., Okayama, Japan, and 5 parts by weight of salt were passed through a sieve to mix sufficiently, and the mixture was admixed and stirred with 1,400 parts by weight of fresh eggs, and 600 parts by weight of a syrup rich in fructosyltrehalose obtained by the method in Example A-10, and further admixed gradually with 5,000 parts by weight of a boiling milk. The resulting mixture was heated gently while stirring, and the heating was stopped when the whole contents completely gelatinized and became semitransparent, then cooled and mixed with an adequate amount of a vanilla flavor to obtain a custard cream.

The product has a smooth surface and a pleasant taste with an adequate sweetness. Because the product exerts a growth-promoting activity for bifid bacteria, it can be arbitrarily used in the maintenance and promotion of health and beauty, the prevention of geriatric diseases, and the promotion of recovery of health during and after diseases.

EXAMPLE B-7
Premix of corn potage soup

Thirty parts by weight of pregelatinized-corn powder, 5 parts by weight of pregelatinized-starch, 4 parts by weight of pregelatinized-potato starch, 12 parts by weight of pregelatinized-waxy corn starch, 8 parts by weight of a powder rich in fructosyltrehalose obtained by the method in Example A-11, 5 parts by weight of sodium glutamate, 8.5 parts by weight of salt, 7 parts by weight of skim milk powder, and 0.5 part by weight of an onion powder were mixed and ground sufficiently, and the mixture was admixed with a mixture of 0.5 part by weight of sorbitan fatty acid ester and 9 parts by weight of plant hardened oil which had been melted by heating, and further mixed with 10 parts by weight of lactose. The resulting mixture was placed in a fluidized-bed granulator, granulated by spraying a small amount of water, dried with air heated to 70° C., and sieved to obtain the desired product.

The product readily dissolves and disperses in hot water into a tastable soup. Because the product exerts a growth-promoting activity for bifid bacteria and a mineral absorption-promoting activity, it can be arbitrarily used in the maintenance and promotion of health and beauty, the prevention of geriatric diseases, and the promotion of recovery of health during and after diseases.

EXAMPLE B-8
Milky lotion

A half part by weight of polyoxyethylene behenyl ether, one part by weight of polyoxyethylene sorbitol tetraoleate, one part by weight of glyceryl monostearate, lipophilic, 0.5 part by weight of behenyl alcohol, one part by weight of avocado oil, 3.5 parts by weight of an erlose syrup obtained by the method in Example A-5, one part by weight of α-glycosyl rutin, and adequate amounts of vitamin E and an antiseptic were dissolved by heating in a conventional manner. The mixture was admixed with 5 parts by weight of 1,3-butylene glycol, 0.1 part by weight of carboxy vinyl polymer, and 85.3 parts by weight of refined water, and the resulting mixture was emulsified by a homogenizer into a milky lotion.

The product is a milk lotion with a satisfactory humectancy and can be arbitrarily used as a sunscreen or a skin-whitening agent.

EXAMPLE B-9
Skin cream

Two parts by weight of polyoxyethylene glycol monostearate, 5 parts by weight of glyceryl monostearate, self-emulsifying, 2 parts by weight of α-glycosyl rutin, one part by weight of liquid petrolatum, 10 parts by weight of glyceryl tri-2-ethylhexanoate, 4 parts by weight of a syrup containing fructosyltrehalose obtained by the method in Example A-9, and an adequate amount of an antiseptic were dissolved by heating in a conventional manner. The solution was admixed with 5 parts by weight of 1,3-butylene glycol and 66 parts by weight of refined water, and the resultant mixture was emulsified by a homogenizer and admixed with an adequate amount of a flavor while stirring to obtain a cosmetic cream.

The product having a sufficient spreadability can be arbitrarily used as a sunscreen, a skin-refining agent or a skin-whitening agent.

EXAMPLE B-10
Tooth paste

A tooth paste was obtained by mixing 13 parts by weight of water with 45 parts by weight of calcium secondary phosphate, 1.5 parts by weight of sodium lauryl sulfate, 25 parts by weight of glycerine, 0.5 part by weight of polyoxyethylene sorbitan laurate, 15 parts by weight of xylosylfructoside obtained by the method in Example A-8, 0.02 part by weight of saccharine, and 0.05 part by weight of an antiseptic.

The product is a satisfactory tooth paste because it imparts a satisfactory gloss to the teeth and exerts an effective detergency.

EXAMPLE B-11
Nutrient for intubation feeding

A nutritional composition was prepared by mixing 20 parts by weight of a powder rich in erlose obtained by the method in Example A-6, 1.1 parts by weight of glycine, one part by weight of sodium glutamate, 0.4 part by weight of calcium lactate, 0.1 part by weight of magnesium carbonate, 0.01 part by weight of thiamine, and 0.01 part by weight of riboflavin. Twenty-four g aliquots of the nutritive composition were injected into small laminated-aluminum-bags which were then heat sealed to obtain the desired product.

One bag is dissolved in about 300–500 ml water into a nutritional solution before administered to the nasal cavity and stomach by the intubation feeding.

The product can be arbitrarily used as a parenteral nutritional solution for humans and domestic animals.

EXAMPLE B-12
Nutrient for intubation feeding

A nutritional composition was prepared by mixing 580 parts by weight of a powder rich in lactosucrose obtained by the method in Example A-4, 190 parts by weight of dried yolks, 209 parts by weight of skim milk powder, 4.4 parts by weight of sodium chloride, 1.85 parts by weight of potassium chloride, 4 parts by weight of magnesium sulfate, 0.01 part by weight of thiamine, 0.1 part by weight of sodium ascorbate, 0.6 part by weight of vitamin E acetate, and 0.04 part by weight of nicotinamide. Twenty-five g aliquots of the nutritional composition were injected into small laminated-aluminum-bags which were then heat sealed to obtain a solid nutrient for intubation feeding.

The product has a relatively long shelf life and a sufficient solubility and dispersibility. In use, one bag of the product is dissolved in about 150–300 ml water into a nutrient solution before administered to the nasal cavity, gullet or stomach. The product exerts a growth-promoting activity for bifid bacteria and a mineral absorption-promoting activity and can be arbitrarily used in the maintenance and promotion of health and beauty, the prevention of geriatric diseases, the promotion of recovery of health during and after diseases, and the treatment and/or the prevention of diseases. Furthermore, the product can be arbitrarily used to promote the growth of domestic animals and poultry and to promote the recovery of health during and after diseases.

EXAMPLE B-13
Tablet

Forty parts by weight of a powder rich in fructosyltrehalose obtained by the method in Example A-11, 10 parts by weight of maltose, one part by weight of calcium tertiary phosphate, one part by weight of sugar ester, and an adequate amount of a powdery flavor were mixed to homogeneity, and the mixture was tabletted by a tabletting machine to obtain tablets, about 350 mg each.

The product is a readily swallowable and stable tablet free of cracking. A dose of about 1–40 tablets/day/adult, preferably, about 2–20 tablets/day/adult exerts a satisfactory growth-promoting activity for bifid bacteria and an effective mineral absorption-promoting activity. Thus the product can be arbitrarily used in the maintenance and promotion of health and beauty, the prevention of geriatric diseases, the promotion of recovery of health during and after diseases, and the treatment and/or the prevention of diseases.

EXAMPLE B-14

Interferon tablet

A natural human interferon-α preparation, produced by Hayashibara Biochemical Laboratories, Inc., Okayama, Japan, and commercialized by Cosmo Bio, Tokyo, Japan, was in a conventional manner fed to a column of an immobilized anti-human interferon-αantibody to adsorb the interferon-α. A buffer containing calf serum albumin as a stabilizer was fed to the column, followed by removing an excessive amount of the albumin from the column. Thereafter, the interferon-α was eluted from the column with a physiological saline containing 5% of a powder rich in lactosucrose obtained by the method in Example A-4. The eluate was membrane filtered, and the filtrate was dehydrated by the addition of about 20-fold volumes of "FINETOSE®", an anhydrous crystalline maltose powder commercialized by Hayashibara Shoji, Inc., Okayama, Japan, followed by pulverizing the dehydrated product, and tabletting the resulting powder by a tabletting machine to obtain tablets containing about 150 units of the natural human interferon-α per tablet, about 200 mg weight.

The product can be orally administered to patients as a sublingual tablet at a dose of 1–10 tablets/day/adult, and arbitrarily used to treat viral diseases, allergies, rheumatisms, diabetes, and malignant tumors. More particularly, the product can be suitably used as a therapeutic agent for AIDS and hepatitis, the number of patients suffering from these diseases has been remarkably increasing. The lactosucrose and maltose incorporated in the product stabilize the natural human interferon-α to give a relatively long shelf life even when stored at ambient temperatures.

EXAMPLE B-15

Formula feed

A formula feed was prepared by mixing 40 parts by weight of powdered wheat bran, 38 parts by weight of skim milk powder, 12 parts by weight of a powder rich in fructosyl-trehalose obtained by the method in Example A-11, 10 parts by weight of a vitamin agent, 5 parts by weight of fish meal, 5 parts by weight of calcium secondary phosphate, 3 parts by weight of a liquid oil and fat, 3 parts by weight of calcium carbonate, 2 parts by weight of salt, and 2 parts by weight of a mineral agent.

The product is a feed with an improved taste preference for domestic animals and poultry, especially, for infant pigs. Because the product exerts a satisfactory growth-promoting activity for bifid bacteria and an effective mineral absorption-promoting activity, it can be arbitrarily used to prevent breeding animals from infectious diseases, prevent diarrhea and unpleasant feces' smell, and promote appetite and fattening. If necessary, the product can be used together with other feed materials such as concentrate materials including grains, wheat flour, starch, oil meals, and chaff and bran, as well as material roughages such as rice and wheat straws, hay, bagasse, and corncob.

As is described above, the present invention relates to a novel bacterial β-fructofuranosidase which has a relatively high fructosyl-transferring activity and can be used on an industrial scale, its preparation and uses. The β-fructofuranosidase forms reducing and non-reducing saccharides using sucrose as a donor. The formed fructosyl-transferred saccharides have the following properties; a pleasant taste and sweetness, osmosis-controlling ability, humectancy, gloss-imparting ability, crystallization-preventing ability, retrogradation-preventing ability, anti-cariogenicity, growth-promoting activity for bifid bacteria, and the mineral absorption-promoting activity. Because of these properties the saccharides can be selectively used in food products, cosmetics and pharmaceuticals. Thus the present invention will greatly contribute to the food, cosmetic, and pharmaceutical industries.

While there has been described what is at present considered to be the preferred embodiments of the invention, it will be understood the various modifications may be made therein, and it is intended to cover in the appended claims all such modifications as fall within the true spirits and scope of the invention.

We claim:

1. A biologically pure culture of a microorganism of the genus Bacillus which forms an isolated β-fructofuranosidase having the following physicochemical properties:
   (1) Action
       Releasing fructose when hydrolizing the β-fructofuranosidic linkage of sucrose, raffinose, and erlose; using these saccharides as saccharide donors, it catalyzes the transfer of β-fructofuranosyl residue to an acceptor selected from the group consisting of other saccharides, sugar alcohols, and alcohols;
   (2) Molecular weight
       49,000±5,000 daltons on sodium dodecyl sulfate polyacrylamide gel electrophoresis (SDS-PAGE);
   (3) Isoelectric point (pI)
       4.6±0.5 on electrophoresis using ampholyte;
   (4) Optimum pH
       A pH of about 5.5–6.0 when incubated at 40° C. for ten minutes;
   (5) Optimum temperature
       About 45° C. and about 50° C. in the absence of and in the presence of calcium ion, respectively, when incubated at pH 6.0 for ten minutes;
   (6) pH stability
       Stable at a pH of about 5.0–8.0 when incubated at 4° C. for 24 hours; and
   (7) Thermal stability
       Stable up to a temperature of about 45° C. when incubated at pH 6.0 for an hour.

2. The culture of claim 1, wherein said microorganism is Bacillus sp. V230 (FERM BP-5054).

3. Bacillus sp. V230 (FERM BP-5054) isolated from soil which produces a β-fructofuranosidase having the following physicochemical properties:
   (1) Action
       Releasing fructose when hydrolizing the β-fructofuranosidic linkage of sucrose, raffinose, and erlose; using these saccharides as saccharide donors, it catalyzes the transfer of β-fructofuranosyl residue to an acceptor selected from the group consisting of other saccharides, sugar alcohols, and alcohols;
   (2) Molecular weight
       49,000±5,000 daltons on sodium dodecyl sulfate polyacrylamide gel electrophoresis (SDS-PAGE);

(3) Isoelectric point (pI)

4.6±0.5 on electrophoresis using ampholyte;

(4) Optimum pH

A pH of about 5.5–6.0 when incubated at 40° C. for ten minutes;

(5) Optimum temperature

About 45° C. and about 50° C. in the absence of and in the presence of calcium ion, respectively, when incubated at pH 6.0 for ten minutes;

(6) pH stability

Stable at a pH of about 5.0–8.0 when incubated at 4° C. for 24 hours; and (7) Thermal stability Stable up to a temperature of about 45° C. when incubated at pH 6.0 for an hour.

* * * * *